United States Patent [19]

Kimura et al.

[11] 4,364,876
[45] Dec. 21, 1982

[54] NOVEL 2-CYANOACRYLATE, PROCESS FOR PRODUCING SAME AND CURABLE COMPOSITION COMPRISING SAME

[75] Inventors: Kaoru Kimura, Kuroishi; Kazuyuki Sakabe, Tokai, both of Japan

[73] Assignee: Toagosei Chemical Industry Co., Ltd., Tokyo, Japan

[21] Appl. No.: 244,276

[22] Filed: Mar. 16, 1981

[30] Foreign Application Priority Data

Mar. 27, 1980 [JP] Japan .................................. 55-38174

[51] Int. Cl.$^3$ ......................................... C07C 121/30
[52] U.S. Cl. ............................... 260/465.4; 260/464; 260/465 D; 526/312
[58] Field of Search .................................. 260/465.4

[56] References Cited

U.S. PATENT DOCUMENTS

| | | | |
|---|---|---|---|
| 2,784,215 | 3/1957 | Joyner | 260/465.4 |
| 3,142,698 | 7/1964 | Halpern et al. | 260/465.4 |
| 3,465,027 | 9/1969 | Hawkins | 260/464 |
| 3,540,126 | 11/1970 | Chang et al. | 260/465.4 X |
| 3,564,078 | 2/1971 | Wicker, Jr. et al. | 260/881 |
| 3,577,394 | 5/1971 | Harrington | 260/78.4 |
| 3,699,127 | 10/1972 | O'Sullivan et al. | 260/33.2 |
| 3,975,422 | 8/1976 | Buck | 260/465.4 |

OTHER PUBLICATIONS

Kulkarn; et al., Journal of Applied Polymer Science, vol. 17, pp. 3509–3514, (1973).

*Primary Examiner*—Joseph Paul Brust
*Attorney, Agent, or Firm*—Cooper, Dunham, Clark, Griffin & Moran

[57] ABSTRACT

2-Cyanoacrylate represented by the formula:

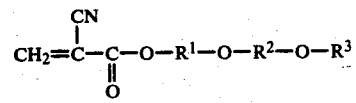

wherein $R^1$ is a 1,2-alkylene group having 2–4 carbon atoms; $R^2$ is an alkylene group having 2–4 carbon atoms and $R^3$ is an alkyl group having 1–6 carbon atoms, said 2-cyanoarylates can be anion-polymerized with a slight quantity of water similarly to hitherto known 2-cyanoacrylates, and the resulting cured product is richer in flexibility than the hitherto known ones. Therefore, it is not only useful as an instant-setting adhesive for metals, plastics, wood and ceramics but also is particularly useful as an adhesive for flexible materials such as rubber, leather, cloth and fiber. Further, said 2-cyanoacrylates are also useful as a coating material and a molding material.

3 Claims, No Drawings

NOVEL 2-CYANOACRYLATE, PROCESS FOR PRODUCING SAME AND CURABLE COMPOSITION COMPRISING SAME

This invention relates to a novel 2-cyanoacrylate, a process for producing the same and a curable composition comprising it.

Hitherto, alkyl 2-cyanoacrylate monomers have widely been utilized for bonding metals, plastics, rubbers, wood, ceramics and the like as a cold-setting one-pack type instant-setting adhesive anion-polymerizable with the very small quantity of water adsorbed on the surface of an adherend.

However, in bonding rubbers, leathers, papers, cloths, fibers and the like, they have had a fault that the cured product (polymer) of the alkyl 2-cyanoacrylate is very hard, and therefore, the bonded part becomes hard and lacks flexibility.

Thus, in order to make the cured product of an alkyl 2-cyanoacrylate type adhesive flexible, the addition of fine rubber particles, the addition of a plasticizer or a thickening agent, or the like have been proposed. However, a bonded part rich in flexibility is not obtainable by these methods.

Improving the flexibility of cured product of an adhesive by changing the kind of the alcohol moiety of 2-cyanoacrylate can be predicted from the case of alkyl acrylate polymer. That is, it is known that the higher the alcohol moiety of the alkyl acrylate, the more flexible the polymer formed becomes, and the most flexible polymer among the alkyl acrylate polymers is an n-octyl acrylate polymer. If this idea is applied to alkyl 2-cyanoacrylates to investigate the properties of higher alkyl 2-cyanoacrylate polymers, they are not flexible polymers but rather brittle polymers. That is, since the alkyl 2-cyanoacrylate polymers are polymers of 1,1-disubstituted vinyl compounds and the substituents thereof are a nitrile group and a carboxyl group, both having a very high polarity, the polymers are very rigid, linear polymers and it is inferred that a mere introduction of a higher alkyl group into the side chain of the polymer cannot render the polymer flexible. The same is also applicable to the case where the polymer is used as a paint, a coating material, a resist, a binder or the like.

The present inventors have conducted extensive research on a modification of such conventional rigid 2-cyanoacrylates to obtain a flexible cured product. As a result, they have succeeded in obtaining a 2-cyanoacrylate which can be cured to give a flexible product, by introducing a group having an affinity to the main chain structure of the cured product of 2-cyanoacrylate which is a rigid, 1,1-disubstituted vinyl polymer and having a plasticizing effect, into the side chain of the polymer.

According to this invention, there is also provided a 2-cyanoacrylate represented by the formula (I):

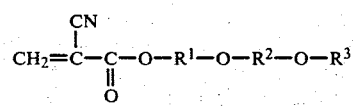

wherein $R^1$ is a 1,2-alkylene group having 2–4 carbon atoms, $R^2$ is an alkylene group having 2–4 carbon atoms and $R^3$ is an alkyl group having 1–6 carbon atoms.

According to this invention, there is also provided a curable composition comprising a stabilizer and the 2-cyanoacrylate represented by the above-mentioned formula (I) or a mixture of said 2-cyanoacrylate and other 2-cyanoacrylate monomer represented by the formula (II):

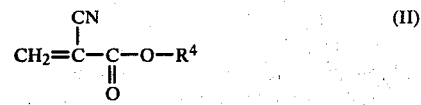

wherein $R^4$ is an alkyl group having 1–12 carbon atoms, an alkenyl group, an alkinyl group, a cycloalkyl group, an aryl group, an aralkyl group or an alkoxyalkyl group; said alkyl, alkenyl, alkinyl, cycloalkyl, aryl and aralkyl groups may optionally have a halogen substituent or an ether linkage; and said alkoxyalkyl group may have a halogen substituent. Examples of the group $R^4$ include methyl, ethyl, n-propyl, isopropyl, n-butyl, isobutyl, pentyl, hexyl, methoxyethyl, ethoxyethyl, butyloxyethyl, methoxypropyl, methoxybutyl, tetrahydrofurfuryl, allyl, propargyl, cyclohexyl, benzyl, 2-chlorethyl, trifluorethyl and the like. As the above-mentioned other 2-cyanoacrylate monomer, all the usually known 2-cyanoacrylates may be used.

When it is intended that the curable composition of this invention be cured by anionic polymerization with moisture, it can serve as an adhesive. When it is intended that an anion-polymerization initiator or a radical polymerization initiator be allowed to be present in the composition, the composition can be applied as paints, various coating materials and molding materials.

In these cases, the following polymer is formed to cause curing:

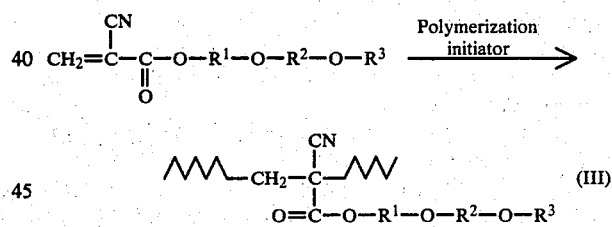

Hitherto, 2-cyanoacrylates have been produced by reacting a cyanoacetate with formaldehyde in the presence of a basic catalyst such as a secondary amine, a sodium alkoxide or the like to prepare a condensate having a degree of condensation of 5–50, and thermally depolymerizing the condensate at 150°–200° C. in the presence of $P_2O_5$ or the like. The novel 2-cyanoacrylate represented by the formula (I) of this invention can also be produced by a processs similar to the hitherto known one.

The cyanoacetate used in this invention as a starting material is obtained by esterification of cyanoacetic acid with an alcohol or by transesterification between an alkyl cyanoacetate and an alcohol, as shown in the following schemes:

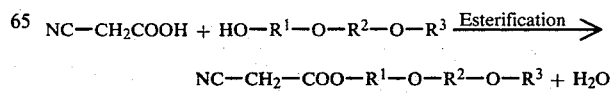

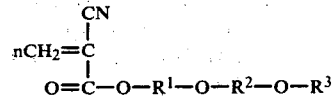

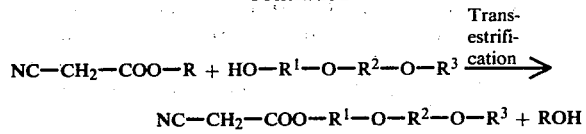

Concrete examples of the alcohol represented by HO—R¹—O—R²—O—R³ used in this invention include diethylene glycol monomethyl ether, diethylene glycol monoethyl ether, diethylene glycol monopropyl ether, diethylene glycol monopentyl ether, diethylene glycol monohexyl ether, dipropylene glycol monomethyl ether, dipropylene glycol monoethyl ether, dipropylene glycol monopropyl ether, dipropylene glycol monobutyl ether, dipropylene glycol monopentyl ether, dipropylene glycol monohexyl ether, dibutylene glycol monomethyl ether, dibutylene glycol monoethyl ether, dibutylene glycol monobutyl ether, mono(3-methoxypropyl)-ethylene glycol, mono(3-methoxybutyl)-ethylene glycol, mono(3-methoxypropyl)-propylene-1,2-glycol, mono(3-methoxybutyl)-propylene-1,2-glycol, mono(methoxyethyl)-propylene-1,2-glycol, mono(methoxyethyl)-butylene-1,2-glycol and the like.

A cyanoacetate of the above-mentioned alcohol and formaldehyde or paraformaldehyde are condensed in the presence of a catalyst at a molar ratio of 0.5–1.5:1, preferably 0.8–1.2:1, to obtain a condensate. The catalyst is a base or an amine such as piperidine, diethylamine, dibutylamine, morpholine, KOH, NaOH, sodium alkoxide, secondary amine salt or the like, which is used in an amount of 0.001–10 mole%, preferably 0.01–1 mole%, based on the cyanoacetate. As the solvent for the reaction, there may be used benzene, toluene, xylene, trichloroethylene, methylchloroform, tetrahydrofuran, ethanol, butanol, water or the like. When the reaction is carried out at a temperature of 20°–150° C., preferably 50°–130° C., a condensate having a degree of condensation of about 5–50 is obtained with formation of condensation water.

Then, this condensation reaction mixture is depolymerized either directly or after removal of the condensation catalyst. The depolymerization is carried out at a reaction temperature of 140°–250° C. at a pressure of 0.1–50 mmHg in the presence of 0.01–10% by weight of phosphorus pentoxide, phosphoric acid, condensed phosphoric acid or the like. The crude cyanoacrylate formed by the depolymerization reaction is again distilled, whereby the cyanoacrylate of this invention having a high purity is obtained.

The above-mentioned condensation reaction and the depolymerization reaction can be expressed by the following schemes:

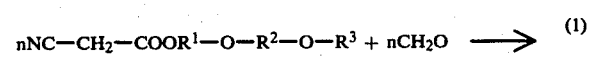  (1)

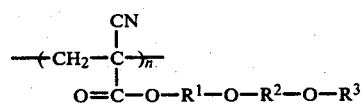

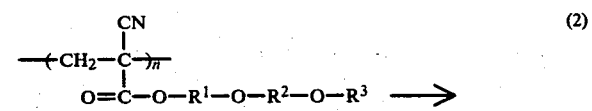  (2)

The novel 2-cyanoacrylate of this invention thus obtained is a monomer having a high purity and a low or medium viscosity which is represented by the formula (I).

The 2-cyanoacrylate of this invention is a novel compound which can be anion-polymerized with a slight quantity of water, an amine, an alkali or the like or can be radical-polymerized with a peroxide or an azo compound similarly to the hitherto known alkyl 2-cyanoacrylates.

Typical concrete examples of the 2-cyanoacrylate represented by the formula (I) are as follows:
2-(2'-methoxy)-ethoxyethyl-2''-cyanoacrylate,
2-(2'-ethoxy)-ethoxyethyl-2''-cyanoacrylate,
2-(2'-propyloxy)-ethoxyethyl-2''-cyanoacrylate,
2-(2'-butoxy)-ethoxyethyl-2''-cyanoacrylate,
2-(2'-pentyloxy)-ethoxyethyl-2''-cyanoacrylate,
2-(2'-hexyloxy)-ethoxyethyl-2''-cyanoacrylate,
2-(2'-methoxy)-propyloxypropyl-2''-cyanoacrylate,
2-(2'-ethoxy)-propyloxypropyl-2''-cyanoacrylate,
2-(2'-propyloxy)-propyloxypropyl-2''-cyanoacrylate,
2-(2'-butyloxy)-propyloxypropyl-2''-cyanoacrylate,
2-(2'-pentyloxy)-propyloxypropyl-2''-cyanoacrylate,
2-(2'-hexyloxy)-propyloxypropyl-2''-cyanoacrylate,
2-(2'-methoxy)-butyloxybutyl-2''-cyanoacrylate,
2-(2'-ethoxy)-butyloxybutyl-2''-cyanoacrylate,
2-(2'-butyloxy)-butyloxybutyl-2''-cyanoacrylate,
2-(3'-methoxy)-propyloxyethyl-2''-cyanoacrylate,
2-(3'-methoxy)-butyloxyethyl-2''-cyanoacrylate,
2-(3'-methoxy)-propyloxypropyl-2''-cyanoacrylate,
2-(3'-methoxy)-butyloxypropyl-2''-cyanoacrylate,
2-(2'-methoxy)-ethoxypropyl-2''-cyanoacrylate,
2-(2'-methoxy)-ethoxybutyl-2''-cyanoacrylate.

The novel 2-cyanoacrylate represented by the formula (I) of this invention has two ether linkages (—C—O—C—) in the alcohol moiety of the ester and is characterized in that the alkylene group (R¹ of formula (I)) to which the 2-cyanoacryloyl group is directly bonded in an ethylene group, a propylene group or a butylene group connected to the adjacent ether linkage at the 1,2-position. Such a 2-cyanoacrylate is easy to synthesize, high in purity, excellent in storage stability and very effective as an adhesive. From the viewpoint of production and practical value, 2-cyanoacrylates wherein R² of the formula (I) is an alkylene group having 2–4 carbon atoms (in this case, the alkylene group may be 1,2-, 1,3- or 1,4-one) and R³ of the formula (I) is an alkyl group having 1–6 carbon atoms are preferred.

When the novel 2-cyanoacrylate represented by the formula (I) of this invention is used to form a curable composition which is used as an adhesive or the like, at least one member selected from the group consisting of hydroquinone, hydroquinone monomethyl ether, catechol, pyrogallol, phenol, Bisphenol A, anisole, 2,6-di-t-butylphenol (BHT), sulfurous acid (SO₂), p-toluenesulfonic acid, methanesulfonic acid, benzenesulfonic acid, trifluoromethanesulfonic acid, trifluoroacetic acid, carbon dioxide gas, thionyl chloride, propane sultone and the like is added as a stabilizer in an amount of 1–10,000 ppm (by weight) and preferably 10–1,000 ppm (by weight).

When the curable composition of this invention is used as a composition having a high viscosity, an adhesive having the desired viscosity can be obtained by dissolving a polymer such as alkyl acrylate polymer, for example, polyalkyl acrylates and copolymers of alkyl acrylate and vinyl acetate, styrene, butadiene, acrylic acid, methacrylic acid, acrylonitrile, methacrylonitrile, glycidyl methacrylate and the like; alkyl methacrylate polymer, for example, polyalkyl methacrylates and copolymers of alkyl methacrylate and vinyl acetate, styrene, butadiene, acrylic acid, methacrylic acid, acrylonitrile, methacrylonitrile, glycidyl methacrylate, and the like; alkyl cyanoacrylate polymer; acetylcellulose, polystyrene or the like into the composition. Usually, an adhesive composition having a viscosity of 1-10,000 cps is used effectively.

Further, a plasticizer may be added if it is necessary. For example, a flexible cured product can be obtained by adding dioctyl phthalate, dibutyl phthalate, trioctyl trimellitate, dioctyl adipate, dioctyl glutarate or the like in an amount of 0-50% by weight based on the weight of the 2-cyanoacrylate.

Further, fine particles of, for example, silica, alumina, silica-alumina, boron nitride, polyethylene, Teflon or the like may be added as a filler to improve the bonding strength and adhesion. For this purpose, a fine particle having a size of 0.001-100μ is added in an amount of 1-30% by weight based on the weight of the 2-cyanoacrylate.

If necessary, a dye or a pigment may be added sometimes. A perfume may also be added for the sake of aromatization.

When an adhesive in the form of a curable composition comprising the 2-cyanoacrylate of the formula (I) of this invention is applied to the surface of an adherend, it is anion-polymerized and cured by the slight quantity of water adsorbed on said surface similarly to the hitherto known alkyl 2-cyanoacrylates, to effect bonding. Unlike the hitherto known 2-cyanoacrylate adhesives, however, this adhesive gives a very flexible cured adhesive so that it is effective for bonding flexible materials such as leather, vinyl sheet, rubber, fiber, paper and the like. That is, there is an advantage that the cured adhesive and the neighborhood of the bonded part become as flexible as the bonded material.

Further, a hitherto known 2-cyanoacrylate represented by the formula (II) may be added to the 2-cyanoacrylate of this invention represented by the formula (I) to improve the strength. In general, a higher blending ratio of the novel 2-cyanoacrylate (I) of this invention gives a higher flexibility, and a higher blending ratio of the hitherto known 2-cyanoacrylate (II) gives a higher hardness to the cured product. The blending ratio of the novel 2-cyanoacrylate (I) of this invention to the hitherto known 2-cyanoacrylate (II) is in the range of 1-100:99-0, preferably 30-100:70-0 by weight.

As mentioned above, the novel 2-cyanoacrylate (I) of this invention or its mixture with a hitherto known 2-cyanoacrylate (II) is anion-polymerized by a slight quantity of water. Similarly to the hitherto known alkyl 2-cyanoacrylates, it can also be anion-polymerized by a base or a weak base such as amines, alkalis, phosphines, sulfides, mercaptans, quaternary ammonium salts, water, alcohols or the like to form a polymer having the following skeleton:

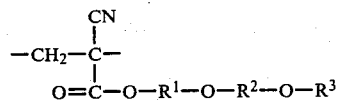

Usually, such a polymer has a molecular weight of about 10,000-1,000,000.

As the initiator for the anionic polymerization, N,N-dimethylaniline, N,N-dimethyl-p-toluidine, sodium ethoxide, triethylbenzylammonium chloride and the like are particularly effective.

If the novel 2-cyanoacrylate (I) of this invention is radical-polymerized with a radical initiator, a cured product having the same skeleton as above is obtained. As the radical initiator, peroxides and azo compounds such as benzoyl peroxide, azobisisobutyronitrile and the like are effective for the radical polymerization of this invention.

Also, it can be polymerized by ultraviolet rays and sunlight rays. In this case, the addition of a photosensitizer such as benzophenone, benzoin monomethyl ether or the like facilitates the photopolymerization.

The novel 2-cyanoacrylate (I) of this invention can also be radical-copolymerized with almost all kinds of vinyl monomers.

The curable composition of this invention comprising the novel 2-cyanoacrylate is useful not only as an adhesive but also as a paint and various coating materials. It can also be used as a molding material or a potting material.

The homopolymer and copolymers of the 2-cyanoacrylate of this invention are also applicable to paints, various coating materials, resists, binders, and the like.

This invention is concretely explained below with reference to Examples which are by way of illustration and not by way of limitation. In the Examples, parts and % are by weight unless otherwise specified.

EXAMPLE 1

Under reflux, 85 parts of cyanoacetic acid, 161 parts of diethylene glycol monoethyl ether, 100 parts of toluene and 1 part of sulfuric acid were subjected to reaction, and the resulting water was removed as an azeotropic mixture with toluene. After completion of the reaction, the unreacted acid was neutralized with sodium hydroxide and the oily phase was distilled to obtain 2-(2'-ethoxy)-ethoxyethyl cyanoacetate. The characteristic properties thereof were as follows: bp=120° C./2 mmHg, $d_4^{20}$=1.098, $n_D^{20}$=1.4448. The yield of the 2-cyanoacetate was 170 parts.

Then, 166 parts of 2-(2'-ethoxy)-ethoxyethyl cyanoacetate, 24 parts of paraformaldehyde, 80 parts of toluene and 0.2 parts of piperidine were subjected to condensation under reflux for 7 hours while removing the water formed. After washing the reaction mixture with an aqueous solution of p-toluenesulfonic acid, the oily phase was separated, mixed with 0.75 part of $P_2O_5$ and 0.5 part of hydroquinone and depolymerized under vacuum at 165°-205° C. Thus, 95 parts of a depolymerized fraction having a boiling point of 120°-146° C./2-3 mmHg was obtained. By distilling it again, 65 parts of 2-(2'-ethoxy)-ethoxyethyl-2''-cyanoacrylate having a boiling point of 107°-110° C./2 mmHg was obtained. It was a light yellow liquid having a viscosity of 20-30 cps. After adding 21 ppm of $SO_2$ thereto, the performances of the product as adhesive were investigated. The results obtained were as follows:

Setting time as measured according to JIS K 6861-1977:
  Iron/Iron: 15 seconds
  Rigid PVC/Riding PVC: 10 seconds
  ABS/ABS: 5 seconds This monomer was anion-polymerized with N,N-dimethyl-p-toluidine to obtain a polymer. The polymer was transparent and had a flexible nature. Its glass transition temperature (Tg) was $-5°$ C.

EXAMPLE 2

Under reflux, 85 parts of cyanoacetic acid, 144 parts of diethylene glycol monomethyl ether, 1 part of sulfuric acid and 100 parts of toluene were subjected to esterification while removing the water formed. Then, the unreacted acid was neutralized and the mixture was distilled to obtain 160 parts of 2-(2′-methoxy)-ethoxyethyl cyanoacetate. The characteristic properties thereof were as follows: bp=120°–122° C./3 mmHg, $d_4^{20}=1.132$, $n_D^{20}=1.4426$.

To condensation were subjected 154 parts of 2-(2′-methoxy)-ethoxyethyl cyanoacetate, 24 parts of paraformaldehyde, 80 parts of toluene and 0.2 part of piperidine under reflux while azeotropically removing the resulting water. After washing the condensation mixture with water, the oily phase was mixed with 0.5 part of $P_2O_5$ and 0.5 part of hydroquinone and depolymerized to obtain 50 parts of a fraction having a boiling point of 100°–148° C./5 mmHg. By distilling it again, 2-(2′-methoxy)-ethoxyethyl-2″-cyanoacrylate having a boiling point of 100°–112° C./3 mmHg was obtained. It was a liquid having a viscosity of 20–30 cps. After adding 21 ppm of $SO_2$ thereto, the performances of the product as adhesive were investigated. The setting time was 10 seconds on rigid polyvinyl chloride and 15 seconds on iron.

EXAMPLE 3

To esterification were subjected 85 parts of cyanoacetic acid, 194 parts of diethylene glycol mono-n-butyl ether, 100 parts of toluene and 2 parts of p-toluenesulfonic acid under reflux while azeotropically removing the water formed, to obtain 195 parts of 2-(2′-n-butyloxy)-ethoxyethyl cyanoacetate. The characteristic properties thereof were as follows: bp=131°–133° C./2 mmHg; $d_4^{20}=1.053$, $n_D^{20}=1.4442$.

Then, 189 parts of 2-(2′-n-butyloxy)-ethoxyethyl cyanoacetate, 24 parts of paraformaldehyde, 80 parts of toluene and 0.2 parts of piperidine were subjected to reaction under reflux while removing the water formed for 7 hours. After washing the condensation reaction mixture with 5% aqueous solution of p-toluenesulfonic acid, the oily phase was separated, mixed with 0.5 part of $P_2O_5$ and 0.5 part of hydroquinone, and depolymerized under vacuum at 150°–200° C. to obtain 88 parts of a fraction having a boiling point of 130°–152° C./3 mmHg. By distilling the fraction again, 2-(2′-n-butyloxy)-ethoxyethyl-2″-cyanoacrylate having a boiling point of 120°–124° C./3 mmHg was obtained. It was a light yellow liquid having a viscosity of 20–30 cps. After adding 53 ppm of $SO_2$ thereto, the performances of the product as adhesive were investigated. The setting time was 45 seconds on rigid polyvinyl chloride and 60 seconds on iron.

EXAMPLE 4

To reaction were subjected 85 parts of cyanoacetic acid, 228 parts of diethylene glycol mono-n-hexyl ether, 1 part of p-toluenesulfonic acid and 150 parts of benzene under reflux while azeotropically removing the water formed. Then, the reaction mixture was neutralized and distilled to obtain 220 parts of 2-(2′-n-hexyloxy)-ethoxyethyl cyanoacetate. The characteristic properties thereof were as follows: bp=152°–145° C./2 mmHg, $d_4^{20}=1.022$, $n_D^{20}$ 1.4465.

Then, 212 parts of 2-(2′-n-hexyloxy)-ethoxyethyl cyanoacetate, 24 parts of paraformaldehyde, 80 parts of toluene and 0.2 part of piperidine were subjected to reaction under reflux while removing the resulting condensation water azeotropically. Then, the reaction product was depolymerized under vacuum at 150°–200° C. in the presence of 0.5 part of $P_2O_5$ and 0.5 part of hydroquinone to obtain 40 parts of a fraction having a boiling point of 143°–160° C./3 mmHg. By distilling the fraction again, 2-(2′-n-hexyloxy)-ethoxyethyl-2″-cyanoacrylate having a boiling point of 130°–135° C./3 mmHg was obtained.

After adding thereto 50 ppm of sulfurous acid gas, the performances of the product as adhesive were investigated. On rigid polyvinyl chloride, the setting time was 30 seconds and the tensile shear strength of bond was 75 kgf/cm².

EXAMPLE 5

To esterification were subjected 85 parts of cyanoacetic acid, 178 parts of dipropylene glycol monomethyl ether, 1 part of sulfuric acid and 100 parts of toluene under reflux while azeotropically removing the water formed. Then, the reaction mixture was distilled to obtain 185 parts 2-(2′-methoxy)-propyloxypropyl cyanoacetate. The characteristic properties of the cyanoacetate were as follows: bp=115°–118° C./2.5 mmHg, $d_4^{20}=1.060$, $n_D^{20}=1.4368$.

Then, 177 parts of 2-(2′-methoxy)-propyloxypropyl cyanoacetate, 24 parts of paraformaldehyde, 80 parts of toluene and 0.2 part of piperidine were subjected to reaction under reflux while azeotropically removing the resulting water. Then, 0.5 part of $P_2O_5$ and 0.5 part of hydroquinone were added to the reaction product thus obtained, and the reaction product was depolymerized in vacuum at 150°–200° C. to obtain 100 parts of a fraction having a boiling point of 110°–130° C./3 mmHg. By distilling the fraction again, 2-(2′-methoxy)-propyloxypropyl-2″-cyanoacrylate having a boiling point of 103°–105° C./3 mmHg was obtained.

It was a colorless liquid. After adding thereto 34 ppm of sulfurous acid gas, the performances of the product as adhesive were investigated. The setting time was 30 seconds on rigid polyvinyl chloride and 45 seconds on iron.

EXAMPLE 6

To a 2-cyanoacrylate monomer as shown in Table 1 was added 2% of N,N-dimethylformamide to prepare a uniform solution. The monomer was anion-polymerized and cured at 40°–60° C. for 12 hours or more to obtain a cured product having a molecular weight of 100,000–300,000 or so as measured by a high speed liquid chromatography (HLC) in tetrahydrofuran. Other properties of the cured products are shown in Table 1.

TABLE 1

$$CH_2=C(CN)-C(=O)-O-R^1-O-R^2-O-R^3$$

Properties of cured products

| $R^1$ | $R^2$ | $R^3$ | Appearance | $T_g$ |
|---|---|---|---|---|
| $-CH_2CH_2-$ | $-CH_2CH_2-$ | $-CH_3$ | Transparent and flexible | — |
| $-CH_2CH_2-$ | $-CH_2CH_2-$ | $-C_2H_5$ | Transparent and flexible | $-5°$ C. |
| $-CH_2CH_2-$ | $-CH_2CH_2-$ | $-n-C_4H_9$ | Transparent and flexible | $-20°$ C. |
| $-CH_2CH_2-$ | $-CH_2CH_2-$ | $-n-C_6H_{13}$ | Transparent and flexible | — |
| $-CH_2CH(CH_3)-$ | $-CH_2CH(CH_3)-$ | $-CH_3$ | Transparent and flexible | $-30°$ C. |

For comparison, ethyl 2-cyanoacrylate was anion-polymerized in the same manner as above to obtain a cured product. It was hard and had a $T_g$ of 100° C. Further, a cured product of n-hexyl 2-cyanoacrylate was also examined. It was hard and brittle.

EXAMPLE 7

To each of the 2-cyanoacrylate monomers shown in Table 1 was added 0.1% of azobisisobutyronitrile. After deaeration, the monomer was radical-polymerized at 60° C. for 24 hours to obtain a cured product. All the cured products obtained were transparent and flexible.

EXAMPLE 8

In 2-(2'-ethoxy)-ethoxyethyl-2''-cyanoacrylate was dissolved 0.2% of benzophenone, and the solution was irradiated with ultraviolet rays from a high pressure mercury lamp in an intert gas atmosphere, such as nitrogen gas. Thus, a transparent cured product rich in flexibility was obtained.

Further, 20 g of 2-(2'-ethoxy)-ethoxyethyl-2''-cyanoacrylate was placed in a polyethylene vessel having a capacity of 20 g and irradiated with sunlight rays. Thus, a transparent and flexible block of 2-(2'-ethoxy)-ethoxyethyl-2''-cyanoacrylate polymer was obtained. The properties thereof were the same as the results of Example 7.

EXAMPLE 9

The 2-(2'-ethoxy)-ethoxyethyl-2''-cyanoacrylate (I) obtained in Example 2 was mixed with ethyl 2-cyanoacrylate (II) in a proportion as shown in Table 2, and 50 ppm of sulfurous acid gas and 1,000 ppm of hydroquinone were added thereto to prepare an adhesive. The bonding performances of the adhesives were measured to obtain the results shown in Table 2.

TABLE 2

| Mixing ratio (by weight) (I)/(II) | Bonding strength (iron/iron) | | |
|---|---|---|---|
| | Tensile shear strength* (kgf/cm²) | Tensile strength** (kgf/cm²) | Impact peel strength (kgf/cm/cm²) |
| 100/0 | 50 | 40 | 11 |
| 70/30 | 120 | 200 | 12 |
| 50/50 | 150 | 260 | 12 |
| 30/70 | 140 | 250 | 9 |
| 0/100 (Control) | 150 | 310 | 7 |

Note:
*Measured according to JIS K 6861-1977
**Measured according to JIS K 6855

EXAMPLE 10

Neoprene rubber was selected as a flexible material. Two pieces of neoprene rubber were bonded to each other with a 2-cyanoacrylate adhesive as shown in Table 3 and the tensile shear strength of bond was measured according to JIS K 6861-1977. The results obtained were as shown in Table 3.

Test piece: neoprene rubber: 3×25×100 mm
Area of bonded surface: 3.125 cm²
Bonding conditions: 23±1° C., 60±2% RH, aging for 24 hours.

TABLE 3

Adhesive: $CH_2=C(CN)-C(=O)-O-R^1-O-R^2-O-R^3$

| $R^1$ | $R^2$ | $R^3$ | Tensile shear strength of bond (kgf/cm²) | State of bonded part |
|---|---|---|---|---|
| $-CH_2CH_2-$ | $-CH_2CH_2-$ | $-CH_3$ | 4* | Rich in flexibility |
| $-CH_2CH_2-$ | $-CH_2CH_2-$ | $-C_2H_5$ | 4* | Rich in flexibility |
| $-CH_2CH_2-$ | $-CH_2CH_2-$ | $-n-C_4H_9$ | 4* | Rich in flexibility |
| $-CH_2CH(CH_3)-$ | $-CH_2CH(CH_3)-$ | $-CH_3$ | 4* | Rich in flexibility |
| $CH_2=C(CN)-COOC_2H_5$ (Control) | | | 4* | Hard |
| $CH_2=C(CN)-COO-n-C_4H_9$ (Control) | | | 4* | Hard |

Note:
*A material failure occurred.

EXAMPLE 11

2-(2'-Ethoxy)-ethoxybutyl cyanoacetate was synthesized in the same manner as in Example 1 by the esterification between cyanoacetic acid and 2-(2'-ethoxy)-ethoxybutanol. It had the following characteristic properties: bp=130°–135° C./2.5 mmHg, $d_n^{20}=1.05$.

Then, 189 parts of 2-(2'-ethyoxy)-ethoxybutyl cyanoacetate, 24 parts of paraformaldehyde, 80 parts of toluene and 0.2 parts of piperidine were condensed in the same manner as in Example 1, and subsequently, the reaction product was depolymerized to obtain 70 parts of a fraction having a boiling point of 135°–150° C./3 mmHg. By distilling the fraction again, 2-(2'-ethoxy)-ethoxybutyl-2''-cyanoacrylate having a boiling point of 122°–125° C./3 mmHg was obtained.

An adhesive obtained by adding 50 ppm of SO₂ thereto had a setting time of 45 seconds on rigid polyvinyl chloride and gave a flexible cured product.

What is claimed is:
1. A 2-cyanoacrylate represented by the formula:

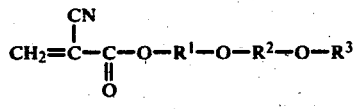

(I)

wherein $R^1$ is a 1,2-alkylene group having 2–4 carbon atoms, $R^2$ is an alkylene group having 2–4 carbon atoms and $R^3$ is an alkyl group having 1–6 carbon atoms.

2. A 2-cyanoacrylate according to claim 1 selected from the group consisting of 2-(2'-methoxy)-ethoxyethyl-2''-cyanoacrylate, 2-(2'-ethoxy)-ethoxyethyl-2''-cyanoacrylate, 2-(2'-propyloxy)-ethoxyethyl-2''-cyanoacrylate, 2-(2'-butyloxy)-ethoxyethyl-2''-cyanoacrylate, 2-(2'-pentyloxy)-ethoxyethyl-2''-cyanoacrylate, 2-(2'-hexyloxy)-ethoxyethyl-2''-cyanoacrylate, 2-(2'-methoxy)-propyloxypropyl-2''-cyanoacrylate, 2-(2'-ethoxy)-propyloxypropyl-2''-cyanoacrylate, 2-(2'-propyloxy)-propyloxypropyl-2''-cyanoacrylate, 2-(2'-butyloxy)-propyloxypropyl-2''-cyanoacrylate, 2-(2'-pentyloxy)-propyloxypropyl-2''-cyanoacrylate, 2-(2'-hexyloxy)-propyloxypropyl-2''-cyanoacrylate, 2-(2'-methoxy)-butyloxybutyl-2''-cyanoacrylate, 2-(2'-ethoxy)-butyloxybutyl-2''-cyanoacrylate, 2-(2'-butyloxy)-butyloxybutyl-2''-cyanoacrylate, 2-(3'-methoxy)-propyloxyethyl-2''-cyanoacrylate, 2-(3'-methoxy)-butyloxyethyl-2''-cyanoacrylate, 2-(3'-methoxy)-propyloxypropyl-2''-cyanoacrylate, 2-(3'-methoxy)-butyloxypropyl-2''-cyanoacrylate, 2-(2'-methoxy)-ethoxypropyl-2''-cyanoacrylate and 2-(2'-methoxy)-ethoxybutyl-2''-cyanoacrylate.

3. A 2-cyanoacrylate according to claim 1 selected from the group consisting of 2-(2'-ethoxy)-ethoxyethyl-2''-cyanoacrylate, 2-(2'-methoxy)-ethoxyethyl-2''-cyanoacrylate, 2-(2'-n-butyloxy)-ethoxyethyl-2''-cyanoacrylate, 2-(2'-n-hexyloxy)-ethoxyethyl-2''-cyanoacrylate and 2-(2'-methoxy)-propyloxypropyl-2''-cyanoacrylate.

* * * * *